(12) United States Patent
Nilsson et al.

(10) Patent No.: US 7,230,096 B2
(45) Date of Patent: Jun. 12, 2007

(54) INHIBITORS AGAINST GALECTINS

(76) Inventors: Ulf Nilsson, S-225, 94 Lund (SE);
Hakon Leffler, S-222, 24 Lund (SE);
Pernilla Sörme, S-226, 49 Lund (SE)

( * ) Notice: Subject to any disclaimer, the term of this patent is extended or adjusted under 35 U.S.C. 154(b) by 469 days.

(21) Appl. No.: 10/466,933

(22) PCT Filed: Jan. 21, 2002

(86) PCT No.: PCT/SE02/00089

§ 371 (c)(1),
(2), (4) Date: Jan. 14, 2004

(87) PCT Pub. No.: WO02/057284

PCT Pub. Date: Jul. 25, 2002

(65) Prior Publication Data

US 2004/0147730 A1    Jul. 29, 2004

(30) Foreign Application Priority Data

Jan. 22, 2001    (SE)    .................................... 0100172

(51) Int. Cl.
*C13K 5/00* (2006.01)
*C07H 3/02* (2006.01)
*C07H 3/04* (2006.01)
*C07H 3/06* (2006.01)

(52) U.S. Cl. ................. 536/123.13; 514/53; 536/123.1
(58) Field of Classification Search ........... 536/123.13; 514/53

See application file for complete search history.

(56) References Cited

FOREIGN PATENT DOCUMENTS

| EP | 0 561 523 A2 | 9/1993 |
| WO | WO 00/07624 | 2/2000 |
| WO | WO00/07624 | * 2/2000 |
| WO | WO 00/29418 | 5/2000 |

OTHER PUBLICATIONS

Lu et al. "Synthesis of a divalent glycoside of an alpha-galactosyl disaccharide epitope involved in the hyperacute rejection of xenotransplantation" (2001) Carbohydrate Research, vol. 334, pp. 289-294.*
Stults et al., "Characterization of the substrate specificity of alpha-1,3-galactosyltransferase utilizing modified N-acetyllactosamine disaccharides." (1999) Glycobiology, vol. 9, No. 7, pp. 661-668.*
The Merck Manual of Diagnosis and Therapy, seventeenth edition, 1999, Published by Merck Research Laboratories, pp. 397-398, 948-949, 1916, and 1979-1981.*
The Oxford Textbook of Oncology, 1995, published by Oxford University Press, pp. 447-453.*

(Continued)

*Primary Examiner*—Shaojia Anna Jiang
*Assistant Examiner*—Eric S. Olson
(74) *Attorney, Agent, or Firm*—Finnegan, Henderson, Farabow, Garrett & Dunner, L.L.P.

(57) ABSTRACT

The present invention relates to novel compounds, the use of said compounds as a medicament as well as for the manufacture of a medicament for treatment of disorders relating to the binding of galectin to receptors in a mammal. Said galectin is preferably a galectin 3.

8 Claims, 4 Drawing Sheets

A

B

Diverse chemical structures

OTHER PUBLICATIONS

Bresalier et al., "Metastasis of Human Colon Cancer is Altered by Modifying Expression of the Beta-Galactoside-Binding Protein Galectin 3" Gastroenterology (1998) vol. 115, pp. 287-296.*

Kiso, M. et al., "Carboymethylgalactose Derivatives", Patent Abstracts of WIPO No. WO 00/17216, (Mar. 30, 2000).

Helland, A. C. et al., "Methyl 3-Amino-3-Deoxy-.Beta.-D-Galactopyranosyl-(1.fwdarw.4)-2-Acetamido-2-Deoxy-.D-Glucopyranoside:an Inhibitor of UDP-D-Galactose: .Beta.-D-Galactopyranosyl-(1.fwdarw.4)-2-Acetamido-2-Deoxy-D-Glucose (1.fwdarw.3)-.Alpha.-D-Galactopyranosyltransferase", CAPLUS Abstract of Carbohydr. Res., vol. 276, No. 1, pp. 91-98, (1995).

Bresalier, R. S. et al., "Metastasis of Human Colon Cancer is Altered by Modifying Expression of the .Beta.-Galactoside-Binding Protein Galectin 3", CAPLUS Abstract of Gastroenterology, vol. 115, No. 2, pp. 287-296, (1998).

* cited by examiner

A

B

Diverse chemical structures 25
(reference)

INHIBITORS AGAINST GALECTINS

CROSS-REFERENCE TO RELATED APPLICATIONS

This application is a national stage application under 35 USC § 371 of PCT/SE02/00089, filed Jan. 21, 2002, which claims benefit under 35 USC § 119(a)–(d) of foreign application SE0100172-6, filed Jan. 22, 2001.

TECHNICAL FIELD OF THE INVENTION

The present invention relates to novel compounds, the use of said compounds as a medicament and for the manufacture of a medicament for the treatment of any disorder relating to the binding of a galectin to receptors in a mammal. The invention also relates to pharmaceutical compositions comprising said novel compounds.

BACKGROUND ART

The galectins are a family of proteins defined by shared sequence elements and by affinity for β-galactosides (Barondes et al., 1994). There are now ten known mammalian galectins (FIG. 1), but biochemical analysis of tissues as well as the accumulation of partial DNA sequences from expressed sequence tags (ESTs) suggest that there are many more (Cooper and Barondes, 1999). Galectins occur at high concentration (usually 0.–1% of total soluble cell protein) in a limited range of cell types, different for each galectin.

All galectins bind lactose and other β-galactosides, but they differ in their affinity for more complex saccharides (Leffler and Barondes, 1986, Barondes et al., 1994). This suggests that galectins may play a role in decoding the information in complex carbohydrates at the cell surface and in the extracellular matrix. A review of the data up to 1999 is given by Leffler (2001). By cross-linking cell-surface and extracellular glycoproteins (e.g. laminin, integrins, and IgE receptors), extracellular galectins are known to modulate cell adhesion and induce intracellular signals. By the adhesion modulation, galectins may play roles in maintenance of tissue integrity and in cancer metastasis. By the signaling activity, galectins may induce a variety of responses including apoptosis in T-lymphocytes, oxidative burst in neutrophil leukocytes, and through these activities be important in inflammation and immune regulation. In addition, galectins may have intracellular functions; there is evidence for binding to intracellular non-carbohydrate ligands, and roles in RNA splicing and modulation of apoptosis have been suggested.

The best studied are galectin-3 and galectin-1. The present invention relates mainly to galectin-3, but its principles may be applicable also to other galectins.

Potential Therapeutic Use of Galectin-3 Inhibitors. Galectin-3 has been implicated in diverse phenomena and, hence inhibitors may have multiple uses. It is easy to perceive this as a lack of specificity or lack of scientific focus. Therefore, the analogy with aspirin and the cyclooxygenases (COX-I and II) is useful. The COXs produce the precursor of a wide variety of prostaglandins and, hence, are involved in a diverse array of biological mechanisms. Their inhibitors, aspirin and other NSAIDs (non-steroid anti-inflammatory drugs), also have broad and diverse effects. Despite this, these inhibitors are very useful medically, and they have several different specific utilities.

So if galectins, like COXs, are part of some basic biological regulatory mechanism (as yet unknown), they are likely to be 'used by nature' for different purpose in different contexts. Galectin inhibitors, like NSAIDs, are not expected to wipe out the whole system, but to tilt the balance a bit.

Inhibition of Inflammation.

There is now ample evidence that galectin-3 is proinflammatory (reviewed by Leffler, 2001). Its expression is induced in macrophages and other cells during inflammation (Perillo et al., 1998). It has various proinflammatory effects on other cells in the inflammatory site (Sano et al., 2000; Karlsson et al., 1998). Galectin-3 gene null-mutant (knock-out) mice have decreased inflammatory responses (Hsu et al., 2000) and knock-out mice of Mac-2BP, a galectin-3 ligand, have increased inflammatory responses (Trahey et al., 1999). Inflammation is a protective response of the body to invading organisms and tissue injury. However, if unbalanced it also frequently is destructive and occur as part of the pathology in many diseases. Because of this there is great medical interest in pharmacological modulation of inflammation. A galectin-3 inhibitor is expected to provide an important addition to the arsenal available for this.

Treatment of Septic Shock.

The idea of a possible role of galectin-3 in septic shock comes from our own studies (Almquist et al., 2001). Briefly the argument goes as follows. It is known that septic shock involves dissemination of bacterial lipopolysaccharide into the blood stream, and that the pathological effects of this are mediated via neutrophil leukocytes (Karima et al., 1999). LPS does not activate the tissue damaging response of the neutrophil. Instead it primes the neutrophil, so that it is converted from unresponsive to responsive to other, presumably endogenous, activators. In septic shock this priming happens prematurely in the blood stream. Endogenous activators could then induce the tissue damaging response in the wrong place and time. Several candidates have been proposed as these endogenous activators, including TNF-alfa. Inhibitors of these have been used in treatment schemes without much success (Karima et al., 1999). Since our own studies indicate that galectin-3 is a good candidate as an endogenous activator of primed neutrophils (Almquist et al., 2001), galectin-3 inhibitors may be very useful in septic shock.

Treatment of Cancer.

There is a whole other body of evidence suggesting that induced expression of galectin-3 (and perhaps other galectins) promote tumour growth and/or metastasis (reviewed by Leffler, 2001). The evidence is on one hand correlatory—more galectin in more malignant tumours. The direct evidence comes from animal models, mainly by Raz et al, but also others. In paired human tumour cell lines (with decreased or increased expression of galectin-3), the one with more galectin-3 gives more tumours and metastasis in nude mice (Bresalier et al., 1998). A polysaccharide, which inhibits galectin-3 can inhibit tumours in vivo (Pienta et al., 1995). Although there may be different explanations for the effects of galectin-3, inhibition of its activities is expected to be beneficial in cancer.

Galectin-1 and galectin-9 have been shown to induce apoptosis in activated T-cells. Also, galectin-1 is frequently over-expressed in low differentiated cancer cells, and galectin-9 (or its relatives galectin-4 and galectin-8) is expressed in certain cancer types. Hence, these galectins might help the tumour to defend itself against the immune response raised by the host (Perillo et al., 1998; Leffler, 2001). Inhibitors of the galectin would be expected to block such an effect and thereby be useful in cancer treatment.

Known Inhibitors

Natural Ligands.

Solid phase binding assays and inhibition assays have identified a number of saccharides and glycoconjugates with the ability to bind galectins (reviewed by Leffler, 2001). All galectins bind lactose with $K_d$ of 0,5–1 mM. The affinity of D-galactose is 50–100 times lower. N-Acetyllactosamine and related disaccharides bind about as well as lactose but for certain galectins up to 10 times better. The best small saccharide ligands for galectin-3 were those carrying blood group A-determinants attached to lactose or lacNAc-residues and were found to bind up to about 50 times better than lactose. Galectin-1 shows no preference for these saccharides.

Larger saccharides of the polylactosamine type have been proposed as preferred ligands for galectins. In solution using polylactosamine carrying glycopeptides, there was evidence for this for galectin-3 but not galectin-1 (Leffler and Barondes, 1986). A modified plant pectin polysaccharide has been reported to bind galectin-3 (Pienta et al., 1995).

The above described natural saccharides that have been identified as galectin-3 ligands are not suitable for use as active components in pharmaceutical compositions, because they are susceptible to acidic hydrolysis in the stomach and to enzymatic degradation. In addition, natural saccharides are hydrophilic in nature and are not readily absorbed from the gastrointestinal tract following oral administration.

Synthetic Inhibitors.

Thiodigalactoside is known to be a synthetic inhibitor approximately as efficient as N-acetyllactosamine (Leffler and Barondes, 1986). Saccharides coupled to amino acids with anti-cancer activity were first identified as natural compounds in serum, but subsequently synthetic analogues have been made (Glinsky et al., 1996). Among them, those with lactose or Gal coupled to the amino acid inhibits galectins but only with about the same potency as the corresponding underivatized sugar. A divalent form of a lactosyl-amino acid had higher potency in a solid phase assay (Naidenko et al., 2000). Starburst dendrimers (André et al, 1999) and glycopolymers (Pohl et al, 1999), made polyvalent in lactose-residues, have been described as galectin-3 inhibitors with marginally improved potency as compared to lactose. The aforementioned synthetic compounds that have been identified as galectin-3 ligands are not suitable for use as active components in pharmaceutical compositions, because they are hydrophilic in nature and are not readily absorbed from the gastrointestinal tract following oral administration. Dendrimers and glycopolymers are too large to be absorbed and large enough to produce immune responses in patients. Furthermore, dendrimers and glycopolymers are susceptible to acidic hydrolysis in the stomach and to enzymatic hydrolysis.

Thus, there is a considerable need within the art of inhibitors against galectin, in particularly to galectin 3.

SUMMARY OF THE INVENTION

Therefore, the present invention relates to a compound having the general formula (I):

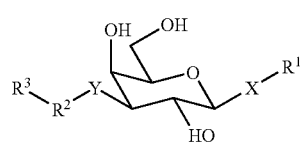

wherein
the configuration of the pyranose ring is D-galacto;
X is selected from the group consisting of O, S, NH, $CH_2$, and $NR^4$, or is a bond;
Y is selected from the group consisting of NH, $CH_2$, and $NR^4$, or is a bond;
$R^1$ is selected from the group consisting of:
a) a saccharide;
b) hydrogen, an alkyl group, an alkenyl group, an aryl group, a heteroaryl group, and a heterocycle;
$R^2$ is selected from the group consisting of CO, $SO_2$, SO, PO, and $PO_2$;
$R^3$ is selected from the group consisting of;
a) an alkyl group of at least 4 carbon atoms, an alkenyl group of at least 4 carbon atoms, an alkyl or alkenyl group of at least 4 carbon atoms substituted with a carboxy group, an alkyl group of at least 4 carbon atoms substituted with both a carboxy group and an amino group, and an alkyl group of at least 4 carbon atoms substituted with a halogen; or
b) a phenyl group, a phenyl group substituted with a carboxy group, a phenyl group substituted with at least one halogen, a phenyl group substituted with an alkoxy group, a phenyl group substituted with at least one halogen and at least one carboxy group, a phenyl group substituted with at least one halogen and at least one alkoxy group, a phenyl group substituted with a nitro group, a phenyl group substituted with a sulfo group, a phenyl group substituted with an amine group, a phenyl group substituted with a hydroxy group, a phenyl group substituted with a carbonyl group and a phenyl group substituted with a substituted carbonyl group; or
c) a phenyl amino group;
$R^4$ is selected from the group consisting of hydrogen, an alkyl group, an alkenyl group, an aryl group, a heteroaryl group, and a heterocycle.

The present invention also relates to a compound according to above-mentioned formula for use as a medicament.

Still further the present invention relates to the use of a compound according to above mentioned formula for the manufacture of a medicament for the treatment of any disorder relating to the binding of a galectin to receptors in a mammal.

Yet further the present invention relates to a pharmaceutical composition comprising a compound according to above mentioned formula as active ingredient together with a pharmaceutically acceptable adjuvant, diluent, excepient or carrier.

Yet further the present invention relates to a method for inhibiting conditions associated with-the binding of galectin to receptors in a mammal which method comprises administering to said mammal an effective amount of a compound according to above mentioned formula.

Still further the present invention relates to a method for inhibiting conditions associated with the binding of galectin to receptors in a mammal which method comprises administering to said mammal an effective amount of a pharmaceutical composition mentioned above Galectin Specificity and Structure.

The studies of galectin specificity using inhibition by small natural saccharides mentioned above indicated that all galectins bound lactose, LacNAc and related disaccharides but that galectin-3 bound certain longer saccharides much better (Leffler and Barondes, 1986) These longer saccharides were characterized by having an additional sugar residue added to the C-3 position of Gal in lactose or LacNAc. The X-ray crystal structure of galectins-1 -2 and -3 demonstrated a highly conserved core binding site for lactose and LacNAc with features in agreement with the specificity studies. (Lobsanov and Rini, 1997; Seetharaman et al., 1998). In addition an extended groove was found which might accommodate the added sugar residue in the longer saccharides. The shape of this grove varies among galectins suggesting that the same extensions would not be bound equally by the different galectins. The galectin-3 CRD structure with bound LacNAc and the extended binding site indicated is shown in FIG. 2.

Design of Galectin Inhibitors Based on Structure and Specificity.

The indication of an extended binding site suggested a possible approach to designing synthetic galectin inhibitors. In this the C-3 of Gal in the core binding site would be modified by a range of structural motifs to produce a collection of diverse chemical structures. The compounds would then be tested in a binding assay for galectins to see which addition created enhanced interaction with the galectins and hence would be a more potent inhibitor. In an initial approach the 3-OH of Gal would be replaced with a 3-NH$_2$ group to facilitate addition of a large array of extensions in a combinatorial chemistry approach. Other routes of derivatization would also be possible.

In the implementation of this strategy the innovative selection of certain chemical additions to the 3'-amino LacNAc, described below, resulted in surprisingly potent inhibitors of galectin-3.

DETAILED DESCRIPTION OF PREFERRED EMBODIMENTS OF THE INVENTION

Figure 1:
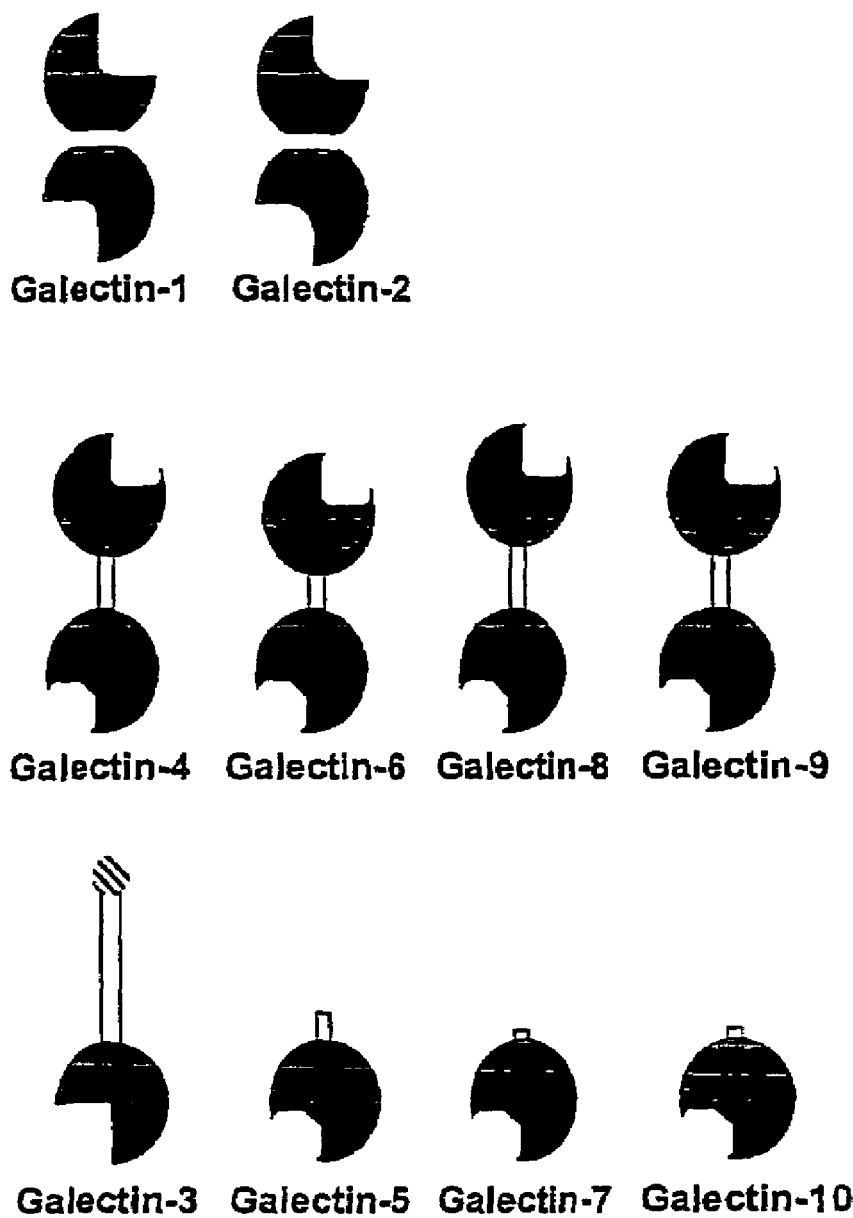
FIG. 1. Schematic picture of galectins. The typical 15 kDa carbohydrate binding domains are filled and other domains are unfilled or hatched (reviewed by Barondes et al., 1994, and by Leffler, 2001).
Figure 2:
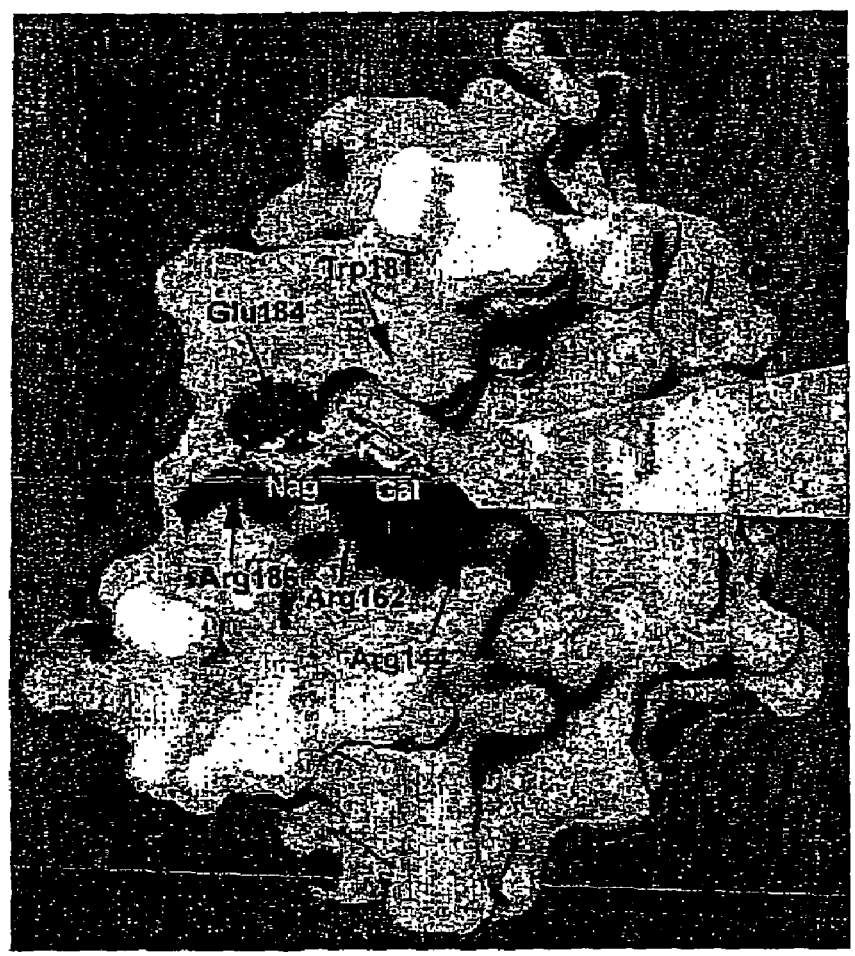
FIG. 2. A) Structure of galectin-3 CRD (shown as smooth surface) with bound LacNAc (stick model) and extended binding site indicated (white semitransparent arrow). The structure with bound LacNAc is from Seetharaman et al. (1998). Major interacting amino acid residues are indicated by black arrows and text. Sugar residues are indicated by grey text (Gal=galactose, Nag=N-acetylglucosamine). The white semitransparent arrow points through the extended binding site at the 3-OH of Gal which is the site of modification discussed in the present invention. B) Schematic of inhibitors based on the strategy in this invention.
Figure 2:
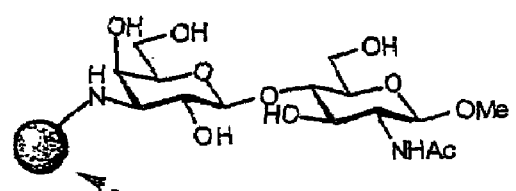

According to one aspect of the invention a compound of above mentioned formula comprises a saccharide (R$^1$=saccharide), which sacharide is selected from the group consisting of glucose, mannose, galactose, N-acetylglucosamine, N-acetylgalactosamine, fucose, fructose, xylose, sialic acid, glucoronic acid, iduronic acid, a disaccharide or an oligosaccharide comprising at least two of the above saccharides, and derivatives thereof. Any other saccharide known to a person skilled within the art may obviously be used as an alternative to the above mentioned saccharides.

In another aspect of the invention, in the above mentioned formula, Y is NH, X is O and said halogen is selected from the group consisting of F, Cl, Br and I. Preferably said halogen is F.

In the present disclosure the term "alkyl group" is meant to comprise from 1 to 12 carbon atoms. Said alkyl group may be straight or branched chain. Said alkyl group may also form a cycle comprising from 3 to 12 carbon atoms.

In the present disclosure the term "alkenyl group" is meant to comprise from 1 to 12 carbon atoms. Said alkenyl group comprises at least one double bond.

In the present disclosure the term "aryl group" is meant to comprise from 4 to 18 carbon atoms. Said aryl group may be a phenyl group or a naphtyl group.

In the present disclosure the term "alkoxy group" is meant to comprise from 1 to 12 carbon atoms. Said alkoxy group may be a methoxy group or an ethoxy group.

In the present disclosure the term "alkylamino group" is meant to comprise from 1 till 12 carbon atoms.

In the present disclosure the term "arylamino group" is meant to comprise from 4 to 12 carbon atoms. Said "arylamino group" may be aniline, carboxylated aniline or halogenated aniline.

In the present disclosure the term "heteroaryl group" is meant to comprise from 4 to 18 carbon atoms, wherein at least one atom of the ring is a heteroatom, i.e. not a carbon. Preferably said heteroatom is N, O or S. Said heteroaryl group may be a pyridine, a pyrrole, a furan or a thiophene.

In the present disclosure the term "heterocycle" is meant to comprise from 1 to 12 carbon atoms in a ring structure, wherein at least one of the atoms in the ring is a heteroatom, i.e. not a carbon. Preferably said heteroatom is O, S or N.

The above mentioned groups may naturally be substituted with any other known substituents within the art of organic chemistry. The groups may also be substituted with two or more of the substituents. Examples of substituents are halogen, alkoxy, nitro, sulfo, amine, hydroxy, and carbonyl groups.

In yet another aspect of the invetion said compound is methyl 2-acetamido-2-deoxy-4-O-(3-[3-carboxypropanamido]-3-deoxy-β-D-galactopyranosyl)-β-D-glucopyranoside (14), methyl 2-acetamido-2-deoxy-4-O-(3-[{Z}-3-carboxypropenamido]-3-deoxy-β-D-galactopyranosyl)-β-D-glucopyranoside (15), methyl 2-acetamido-2-deoxy-4-O-(3-benzamido-3-deoxy-β-D-galactopyranosyl)-β-D- glucopyranoside (16), methyl 2-acetamido-2-deoxy-4-O-(3-[2-carboxybenzamido]-3-deoxy-β-D-galactopyranosyl)-β-D-glucopyranoside (17), methyl 2-acetamido-2-deoxy-4-O-(3-[4-methoxy-2,3,5,6-tetrafluorobenzamido]-3-deoxy-β-D-galactopyranosyl)-β-D-glucopyranoside (18), methyl 2-acetamido-2-deoxy-4-O-(3-[2-carboxy-3,4,5,6-tetrafluorobenzamido]-3-deoxy-β-D-galactopyranosyl)-β-D-glucopyranoside (19), methyl 2-acetamido-2-deoxy-4-O-(3-methane-sulfonamido-3-deoxy-β-D-galactopyranosyl)-β-D-glucopyranoside (20), methyl 2-acetamido-2-deoxy-4-O-(3-[4-nitrobenzenesulfonamido]-3-deoxy-β-D-galactopyranosyl)-β-D-glucopyranoside (21), methyl 2-acetamido-2-deoxy-4-O-(3-phenylaminocarbonylamino-3-deoxy-β-D-galactopyranosyl)-β-D-glucopyranoside (22), methyl 2-acetamido-2-deoxy-4-O-(2-aminoacetamido-3-deoxy-β-D-galactopyranosyl)-β-D-glucopyranoside (23), methyl 2-acetamido-2-deoxy-4-O-(3-[{2S}-2-amino-3-carboxy-propanamido]-3-deoxy-β-D-galactopyranosyl)-β-D-glucopyranoside (24). Preferably said compound is methyl 2-acetamido-2-deoxy-4-O-(3-benzamido-3-deoxy-β-D-galactopyranosyl)-β-D-glucopyranoside (16), methyl 2-acetamido-2-deoxy-4-O-(3-[2-carboxybenzamido]-3-deoxy-β-D-galactopyranosyl)-β-D-glucopyranoside (17), methyl 2-acetamido-2-deoxy-4-O-(3-[4-methoxy-2,3,5,6-tetrafluorobenzamido]-3-deoxy-β-D-galactopyranosyl)-β-D-glucopyranoside (18), or methyl 2-acetamido-2-deoxy-4-O-(3-[2-carboxy-3,4,5,6-tetrafluorobenzamido]-3-deoxy-β-D-galactopyranosyl)-β-D-glucopyranoside (19).

In one aspect the present invention relates to the use of a compound according to above mentioned formula, for the manufacture of a medicament for the treatment of any disorder relating to the binding of a galectin to receptors in a mammal. In one aspect of the invention said galectin is galectin 3.

In another aspect the invention relates to the use of a compound according to above mentioned formula, for the manufacture of a medicament for the treatment of a disorder being selected from the group consisting of inflammation, septic shock, cancer, autoimmune diseases such as reumatoid artrit and multipel schlerosis. Preferably said compound is for the manifacture of a medicament for the treatment of cancer.

In yet another aspect the present invention relates to a pharmaceutical composition comprising a compound according to above mentioned formula as active ingredient together with a pharmaceutically acceptable adjuvant, diluent, excepient or carrier. A pharmaceutical composition of the invention comprises from 1 to 99 weight % of a pharmaceutically acceptable adjuvant, diluent, excepient or carrier and from 1 to 99 weight % of a compound according to above mentioned formula.

In one aspect the invention relates to a method for inhibiting conditions associated with the binding of galectin to receptors in a mammal which method comprises administering to said mammal an effective amount of a compound according to above mentioned formula. In one particularly important aspect of the invention said galectin is a galectin 3.

In another aspect the invention relates to a method for inhibiting conditions associated with the binding of galectin to receptors in a mammal which method comprises administering to said mammal an effective amount of a pharmaceutical composition according to the above. In one particularly important aspect of the invention said galectin is a galectin 3.

The pharmaceutical composition according to the present invention comprising a compound of the invention may be adapted for oral, intravenous, topical, intraperitoneal, nasal, buccal, sublingual, or subcutaneous administration or for administration via the respiratory tract in the form of e.g. an aerosol or an air-suspended fine powder. Therefore, the pharmaceutical composition of the present invention may be in the form of for example tablets, capsules, powders, solutions, transdermal patches or suppositories.

The pharmaceutical composition of the present invention may optionally comprise two or more compounds of the present invention. The composition may also be used together with other medicaments within the art for treatment of related disorders.

The typical dosages of the compounds of the present invention varies within a wide range and depends on many factors such as the route of administration, the requirement of the individual in need of treatment, the individuals body weight, age and general condition.

The adjuvants, diluents, excepients and/or carriers that may be used in the composition of the invention must be pharmaceutically acceptable in the sense of being compatible with the compounds and the other ingredients of the pharmaceutical composition and not deleterious to the recipient thereof. The adjuvants, diluents, excepients and carriers that may be used in the pharmaceutical composition of the invention are well known to a person within the art.

Definitions

IC$_{50}$: Inhibitor concentration that causes 50% inhibition of galectin-3 activity in a defined assay below. K$_{rel}$: Ratio of IC$_{50}$ value of the reference compound methyl 4-O-β-D-galactopyranosyl-2-acetamido-2-deoxy-β-D-glucopyranoside 25 and of IC$_{50}$ value of an inhibitor. ΔΔG: -RTlnK$_{rel}$ (kJ/mol)

Synthesis of the Starting Material

As starting material for the synthesis of novel 3'-amino derivatives of N-acetyllactosamine 12–24 was used methyl 4-O-(2,4,6-tri-O-acetyl-3-azido-3-deoxy-β-D-galactopyranosyl)-2-acetamido-6-O-acetyl-2-deoxy-3-O-stearoyl-β-D-glucopyranoside 10, which was prepared from 1,2,4,6-tetra-O-acetyl-3-azido-3-deoxy-D-galactopyranose 4 (Lowary and Hindsgaul, 1994) and methyl 2-deoxy-2-tetrachlorophthalimido-β-D-glucopyranoside 6 (Stangier and Hindsgaul, 1996) following methods well known to one skilled in the art (Scheme 1). Compound 10 carries a masked 3'-amino group in the form of an azide, as well as a 3-O-stearoyl group to allow purification with C18 solid-phase extraction.

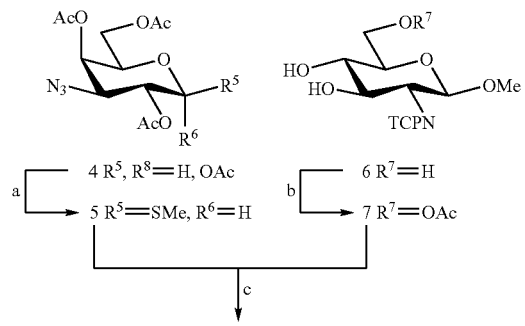

Scheme 1

-continued

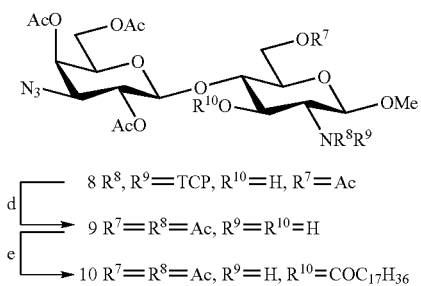

d ⎡ 8 R⁸, R⁹=TCP, R¹⁰=H, R⁷=Ac
  ⎣→ 9 R⁷=R⁸=Ac, R⁹=R¹⁰=H
e  ⎣→ 10 R⁷=R⁸=Ac, R⁹=H, R¹⁰=COC₁₇H₃₆

Scheme 1. a) MeSSiMe₃, TMSOTf, (CH₂Cl)₂, 7 days, 86%. b) AcCl, s-collidine, CH₂Cl₂, −20° C., 7 h, 75%. c) NIS, TfOH, CH₂Cl₂, MS AW-300, −42° C., 2 h, 75%. d) $^i$H₂N(CH₂)₂NH₂, EtOH, 60° C., 7.5 h, then $^{ii}$MeOH, H₂O, Ac₂O, 12 h, 83%. e) C₁₇H₃₆COCl, DMAP, Pyridine, CH₂Cl₂, 24 h, 80%.

Synthesis of the 3-amino Derivatives of N-acetyllactosamine 12–24.

Reduction of the azido group in methyl 4-O-(2,4,6-tri-O-acetyl-3-azido-3-deoxy-β-D-galactopyranosyl)-2-acetamido-6-O-acetyl-2-deoxy-3-O-stearoyl-β-D-glucopyranoside 10 was accomplished by catalytic hydrogenation in ethanol/HCl over Pd/C to give methyl 4-O-(2,4,6-tri-O-acetyl-3-amino-3-deoxy-β-D-galactopyranosyl)-2-acetamido-6-O-acetyl-2-deoxy-3-O-stearoyl-β-D-glucopyranoside 11, which was immediately treated with reagents for amide, sulfonamide and urea formation using methods well known to one skilled in the art (Table 1). Removal of protecting groups according to methods well known to those skilled in the art yielded the 3'-amino derivatives of N-acetyllactosamine 12–24. TABLE 1. Parallel synthesis and spectroscopic data of 3'-amino N-acetyl-lactosamine library (12–24).

TABLE 1

Parallel synthesis and spectroscopic data of 3-amino N-acetyl-lactosamine library (12–24).

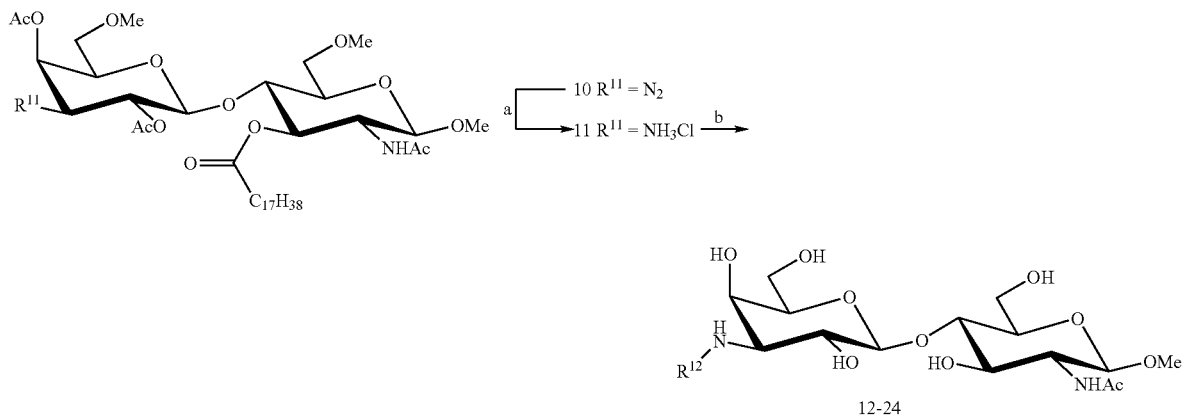

| | Reagent/Condition[b] | R¹² - | Yield (%) | ¹H-NMR data (400 MHz, D₂O) δ | HRMS[c] Calcd/Found |
|---|---|---|---|---|---|
| 12 | None/A[ii](Helland et al. 1995) | H— | 59 | 4.60 (d,1H, J = 8.8 Hz, H-1), 4.48 (d,1H J = 8.3 Hz, H-1) | 397.1822/ 397.1824 |
| 13 | Ac₂O/A | Ac- | 79 | 4.58 (d, 1H , J = 7.8 Hz, H-1), 4.48 (d, 1H, J = 7.7 Hz, H-1), 2.07,2.05 (2s, 3H each, NAc) | 461.1747/ 461.1750 |
| 14 | 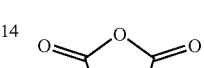/A |  | 100 | 4.58 (d, 1H, J = 7.8 Hz, H-1), 4.48 (d, 1H, J = 7.9 Hz, H-1), 2.55 (m, 2H, CH₂), 2.48 (m, 2H, CH₂) | 519.1802/ 519.1802 |
| 15 | 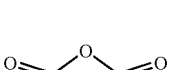/A | 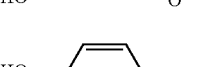 | 32 | 6.37 and 6.12 (2d, 1H each, J = 12.3 Hz, (CH), 4.59 (d, 1H, J = 7.7 Hz,H-1), 4.47 (d, 1H, J = 7.7 Hz,H-1) | 517.1646/ 517.1659 |
| 16 | BzCl/A | 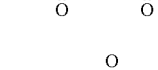 | 24 | 7.83–7.54 (m, 5H, Ar), 4.65 (d, 1H, J = 7.7 Hz.H-1), 4.49 (d, 1H, J = 7.9 Hz, H-1) | 523.1904/ 523.1909 |

TABLE 1-continued

Parallel synthesis and spectroscopic data of 3-amino N-acetyl-lactosamine library (12–24).

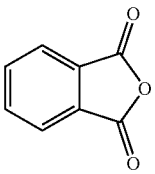

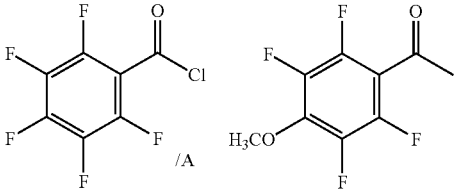

| Reagent/Condition[b] | R[12] - | Yield (%) | $^1$H-NMR data (400 MHz, D$_2$O) δ | HRMS[c] Calcd/Found |
|---|---|---|---|---|
| 17 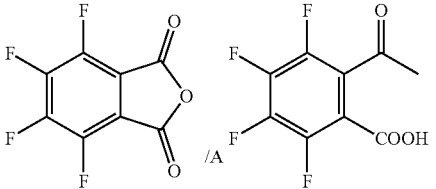 /A | 2-COOH-C$_6$H$_4$-C(O)- | 70 | 7.67–7.51 (m, 4H, Ar), 4.65 (d, 1H, J = 7.8 Hz, H-1), 4.48 (d, 1H, J = 8.1 Hz, H-1) | 567.1802/ 567.1802 |
| 18 pentafluorobenzoyl chloride /A | pentafluorobenzoyl (4-OMe) | 83 | 4.64 (d, 1H, J = 7.9 Hz, H-1), 4.49 (d, 1H, J = 7.9 Hz, H-1) | 625.1633/ 625.1652[d] |
| 19 tetrafluorophthalic anhydride /A | tetrafluoro-2-COOH-benzoyl | 62 | 4.63 (d, 1H, J = 7.7 Hz, H-1), 4.80 (d, 1H, J = 7.0 Hz, H-1) | 661.1245/ 661.1243 |
| 20 CH$_3$SO$_2$Cl/A | CH$_3$SO$_2$— | 10 | 4.55 (d, 1H, J = 6.8 Hz, H-1), 4.47 (d, 1H, J = 8.0 Hz, H-1), 3.16 (s, 3H, Me) | 497.1417/ 497.1415 |
| 21 4-NO$_2$-C$_6$H$_4$-SO$_2$Cl /A | 4-NO$_2$-C$_6$H$_4$-SO$_2$— | 7 | 8.42 (d, 2H, J = 4.9 Hz, Ar), 8.13 (d, 2H, J = 8.5 Hz, Ar-H), 4.45 (d, 1H, J = 7.8 Hz, H-1), 4.44 (d, 1H, J = 7.2 Hz, H-1) | 604.1424/ 604.326[e] |
| 22 PhNCO /A | PhNHC(O)— | 15 | 7.43–7.99 (m, 5H, Ar), 4.61 (d, 1H, J = 7.8 Hz, H-1), 4.48 (d, 1H, J = 7.8 Hz, H-1) | 538.2013/ 538.2022 |
| 23 N-fBoc-glycine/B | H$_2$NCH$_2$CO— | 68 | 4.59 (d, 1H, J = 7.4 Hz, H-1), 4.47 (d, 1H, J = 8.1 Hz, H-1) | 476.1856/ 476.1855 |

TABLE 1-continued

Parallel synthesis and spectroscopic data of 3-amino N-acetyl-lactosamine library (12–24).

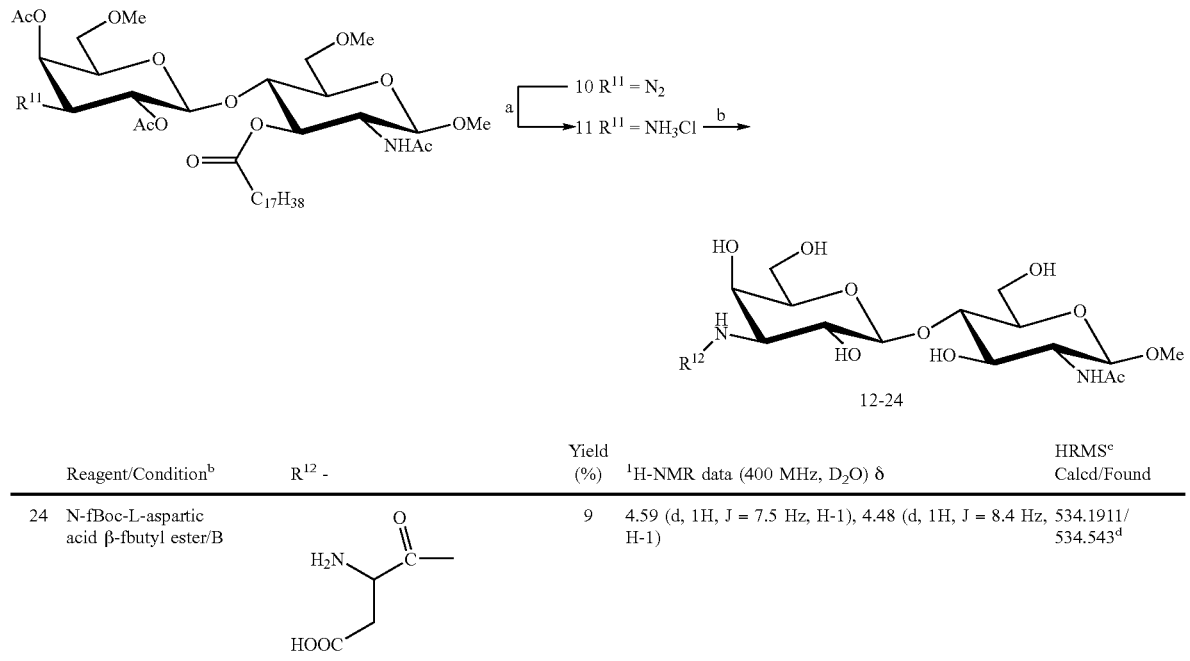

| | Reagent/Condition[b] | R[12] - | Yield (%) | $^1$H-NMR data (400 MHz, D$_2$O) δ | HRMS[c] Calcd/Found |
|---|---|---|---|---|---|
| 24 | N-fBoc-L-aspartic acid β-fbutyl ester/B | | 9 | 4.59 (d, 1H, J = 7.5 Hz, H-1), 4.48 (d, 1H, J = 8.4 Hz, H-1) | 534.1911/ 534.543[d] |

[a]10% Pd/C, H$_2$ (1 atm.), HCl, EtOH, 20 min.
[b]A:[i]pyridine, CH$_2$Cl$_2$, [ii]NaOMe/MeOH. B:[i]DIC, CH$_2$Cl$_2$, [ii]TFA, CH$_2$Cl$_2$, [iii]NaOMe/MeOH.
[c](M + Na)$^+$, except for 12 (M + H)$^+$ and 19 (M − H + 2Na)$^+$.
[d]NaOMe treatment substituted one fluoro with one methoxy group
[e]MALDI-TOF MS

TABLE 2

Relationship between compounds 14–24 and the general structure in claim 1:

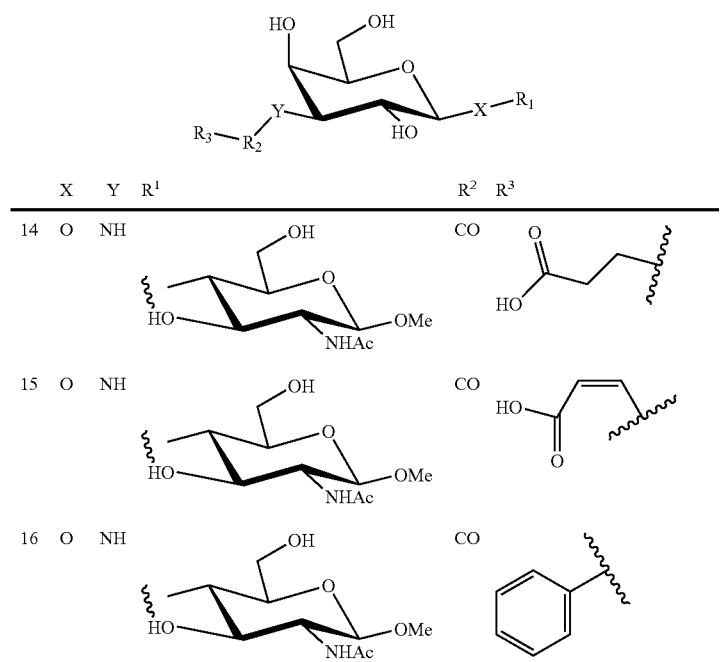

| | X | Y | R[1] | R[2] | R[3] |
|---|---|---|---|---|---|
| 14 | O | NH | (sugar with OH, OMe, NHAc) | CO | (HOOC-CH$_2$-CH$_2$-) |
| 15 | O | NH | (sugar with OH, OMe, NHAc) | CO | (HOOC-CH=CH-) |
| 16 | O | NH | (sugar with OH, OMe, NHAc) | CO | (phenyl) |

TABLE 2-continued
Relationship between compounds 14–24 and the general structure in claim 1:
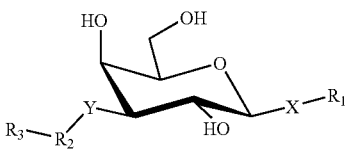
| | X | Y | R¹ | R² | R³ |
|---|---|---|---|---|---|
| 17 | O | NH | 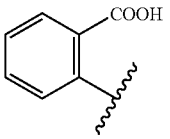 | CO | 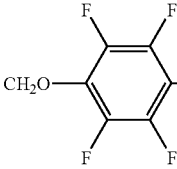 |
| 18 | O | NH | 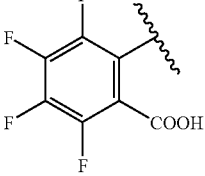 | CO | 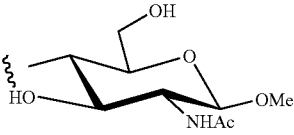 |
| 19 | O | NH | 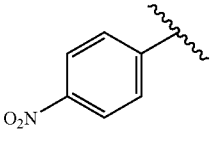 | CO | 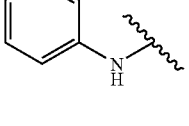 |
| 20 | O | NH | 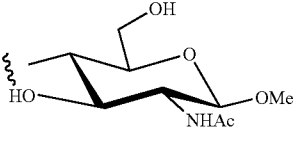 | $SO_3$ | $CH_3-$ |
| 21 | O | NH | 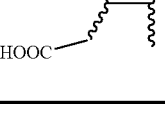 | $SO_3$ | |
| 22 | O | NH | | CO | |
| 23 | O | NH | | CO | $H_3NCH_2-$ |
| 24 | O | NH | | CO | |

Screening Against Galectin-3.

Figure 3:
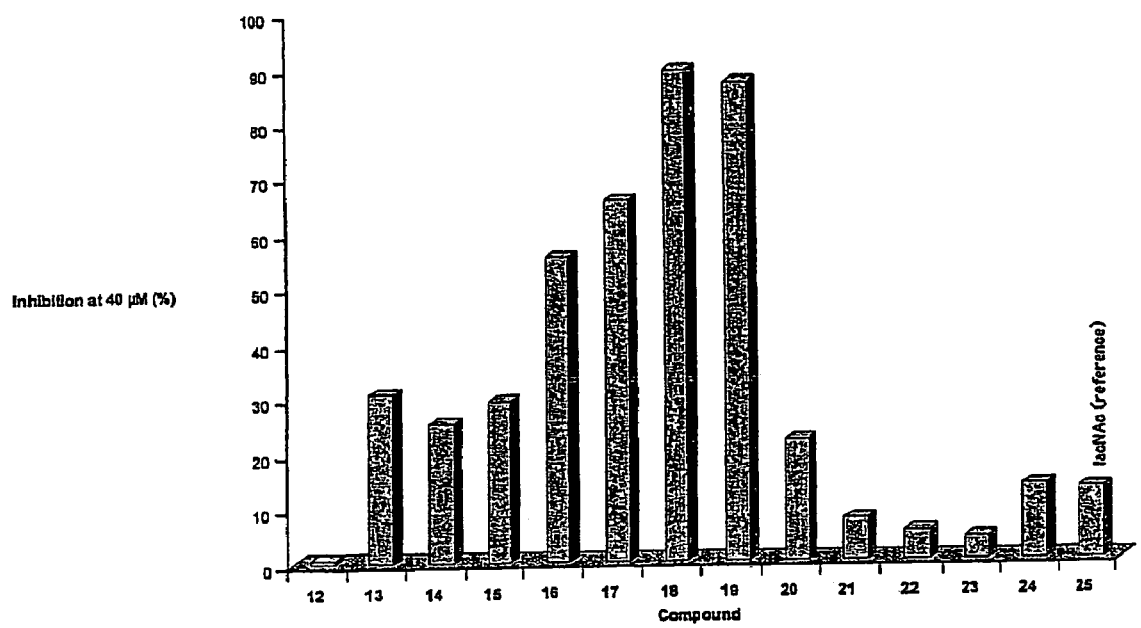
FIG. 3. Screening experiment. Percent inhibition of a Galα3Galβ4GlcNAcβ trisaccharide:horseradish peroxidase conjugate binding to galectin-3 coated microwells at 40 μM inhibitor concentration.
Figure 3:
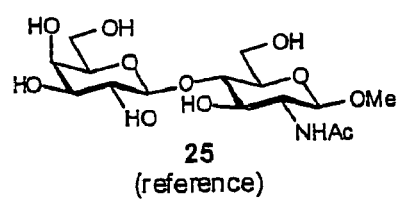

Compounds 12–24 were screened for efficiency in inhibiting galectin-3 binding to a natural receptor (FIG. 3). Compounds 16–19 containing different 3'-benzamide functionalities, showed unexpected high efficiency (55–89% inhibition at 40 μM) as compared to the known reference, inhibitor methyl 4-O-β-D-galactopyranosyl-2-acetamido-2-deoxy-β-D-glucopyranoside 25 (13% inhibition at 40 μM). Other inhibitors were similar (0.7–30% inhibition at 40 μM) to the reference 25. These results were confirmed in an unrelated assay based on fluorescence polarization.

Determination of $IC_{50}$ Values.

Figure 4:
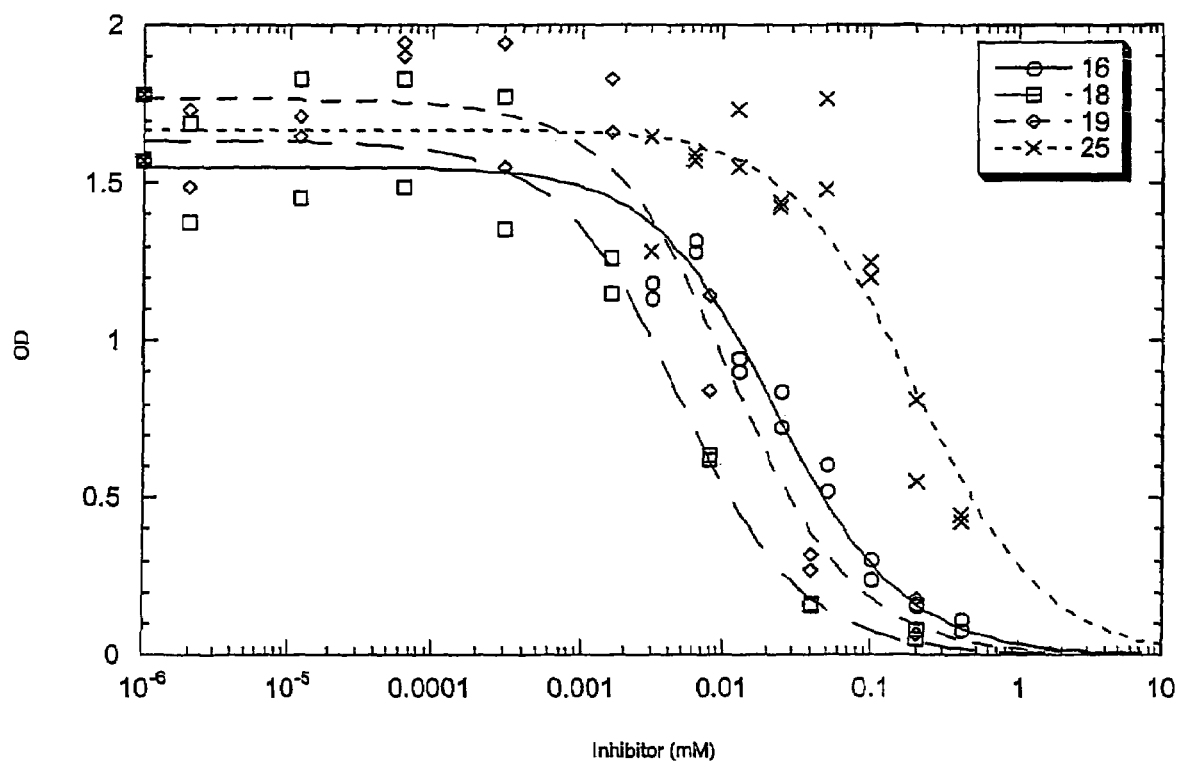
FIG. 4. Determination of IC$_{50}$ values of inhibitors 16, 18, 19 and 25 with competitive inhibition of a Galα3Galβ4GlcNAcβ trisaccharide:horseradish peroxidase conjugate binding to galectin-3 coated microwells.

$IC_{50}$ values of the three best inhibitors, 16, 18–19, identified from screening experiments, and the reference inhibitor 25 were determined by inhibition of galectin-3 with serial dilutions of the inhibitors (FIG. 4). Fluorinated benzamides were up to 41 times as efficient as the known reference inhibitor 25. Compound 18 has an $IC_{50}$ value of 4.8 μM, which is unprecedented in the field of monovalent galectin-3 inhibitors (Table 3). X-Ray crystallography of the galectin-3:18 complex show that the increased affinity for 18 originates in a stacking interaction between the fluorinated benzamide group at C-3' of 18 and arg144 of galectin-3. This beneficial stacking interaction is enabled by an unpredictable move of the arg-144 side-chain by approximately 2.6 Å, as compared to the parent reference galectin-3:25 complex. The unexpectedly high inhibitor potency of 16–19 against galectin-3 renders them suitable as active components in pharmaceutical compositions targeting conditions where galectin-3 plays a pathogenic role. In addition, the unnatural substitutents at C-3 of the galactose residue of compounds 16–19 are expected to improve hydrolytic stability and to improve absorption in the gastro-intestinal tract.

TABLE 3

| | $IC_{50}$ (μM) | $K_{rel}$ |
|---|---|---|
| 16 | 23 | 9 |
| 18 | 4.8 | 41 |
| 19 | 11.2 | 18 |
| 25 | 199 | 1 |

Methodology/Experimental

General Synthetic Procedures

The compounds of this invention may be prepared by the following general methods and procedures. The galectin-3 assays of this invention may be performed by the following general methods and procedures. It should be appreciated that where typical or preferred process conditions (e.g. reaction temperatures, times, molar ratios of reactants, solvents, pressures, pH etc) are given, other process conditions may also be used unless otherwise stated. Optimum reaction conditions may vary with the particular reactants, solvents used and pH etc., but such conditions can be determined by one skilled in the art by routine optimization procedures.

NMR-spectra were recorded with a Bruker DRX-400 instrument. Chemical shifts are given in ppm, with reference to internal CHCl₃ (δ 7.26 ppm) or HDO (δ 4.81 ppm). Chemical shifts and coupling constants were obtained from $^1$H-NMR and proton resonances were assigned from COSY experiments. High-resolution FAB mass spectra (HRMS) were recorded with a JEOL SX-120 instrument. MALDI-TOF Spectra were recorded with a Bruker, Biflex instrument. Column chromatography was performed on SiO₂ (Matrex, 60 Å, 35–70 μm, Grace Amicon) and TLC was carried out on SiO₂ 60 $F_{254}$ (Merck) with detection under UV light and developed with aqueous sulfuric acid. Concentrations were made using rotary evaporation with bath temperature at or below 40° C. CH₂Cl₂ and CH₃CN were dried by distillation from CaH₂. Pyridine was dried over 4 Å molecular sieves. DMF was distilled and dried over 4 Å molecular sieves. MeOH and EtOH were dried over 3 Å molecular sieves. Microwell plates were from Nalge Nunc International (Nunc-immuno plate, maxisorp surface). PBS containing 0.05% Tween 20 is abbreviated PBS-T and PBS-T containing 1% BSA is abbreviated PBSA-T. Recombinant human galectin-3 was produced in *Escherichia coli* and purified as previously described (S. M. Massa et al, 1993). The Galα3Galβ4GlcNAcβ-HRP conjugate (HRP-2) was from Glycorex AB, LUND, SWEDEN. Microwell plates were developed with a TMB-peroxidase substrate kit (BioRad 172–1066) according to the manufacturers recommendations.

Synthesis of Starting Material 10 (Scheme 1).

Methyl 3-azido-3-deoxy-2,4,6-tri-O-acetyl-1-thio-β-D-galactopyranoside (5). To a solution of 4 (Lowary and Hindsgaul, 1994). (231 mg, 0.619 mmol), (methylthio) trimethylsilane (0.250 mL, 1.76 mmol), and molecular sieves AW-300 (0.46 g) in 1,2-dichloroethane (3.0 mL) was added trimethylsilyltrifluromethane sulfonate (0.102 mL, 0.564 mmol) under nitrogen atmosphere. The reaction mixture was stirred at room temperature for 7 days, aqueous Na₂CO₃ (5%., 5 mL) was added, and the mixture was stirred for another 2 hours. The organic layer was separated, washed with water, dried over Na₂SO₄, filtered, and concentrated. The residue was chromatographed (SiO₂, 2:1 heptane-ethylacetate) to give 5 (192 mg, 86%), $[α]_D^{25}$ –34.8° (c 1.0, CHCl₃). $^1$H-NMR data (400 MHz, CDCl₃) δ5.45(dd, 1H, J=3.4, 1.2 Hz, H-4), 5.22 (t, 1H, J=10.0 Hz, H-2), 4.36 (d, 1H, J=9.8 Hz, H-1), 4.15–4.07 (m, 2H, H-6, 6'), 3.91 (dt, 1H, J=6.6, 1.2 Hz, H-5), 3.66 (dd, 1H, J=10.2, 3.4 Hz, H-3), 2.19, 2.17, 2.15 (3 s, 3H each, Ac), 2.06 (s, 3H, Me). HRMS calc. for C₁₃H₁₉N₃NaO₇S (M+Na): 384.0841; found: 384.0837.

Methyl 6-O-acetyl-2-deoxy-2-tetrachlorophthalimido-β-D-glucopyranoside (7). To compound 6 (Stangier and Hindsgaul, 1996) (653 mg, 1.42 mmol) and sym-collidine (0.940 mL, 7.09 mmol) in CH₂Cl₂ (25 mL) under nitrogen atmosphere at –42° C., was added dropwise acetyl chloride (0.115 mL, 1.62 mmol). The reaction was continued at –20° C. for 4 hours, then additional acetyl chloride (0.025 mL, 0.352 mmol) and sym-collidine (0.400 mL, 3.0 mmol) were added. The reaction was quenched with MeOH (8ml) after 3 more hours. The reaction mixture was partitioned between CH₂Cl₂ and aqueous HCl (0.5 M). The organic layer was neutralized with aqueous saturated NaHCO₃, dried over Na₂SO₄, filtered, and concentrated under reduced pressure. The residue was chromatographed (SiO₂, 1:1 heptane-ethylacetate) to give 7 (535 mg, 75%), $[α]_D^{25}$ –18.4° (c 1.0, CHCl₃). $^1$H-NMR data (400 MHz, CDCl₃), δ 5.04 (d, 1H, J=8.5 Hz, H-1), 4.45 (dd, 1H, J=11.9, 2.2 Hz, H-6), 4.27 (dd, 1H, J=11.9, 5.5 Hz, H-6'), 4.19 (dd, 1H, J=10.7, 8.7 Hz, H-3), 3.93 (dd, 1H, J=10.7, 8.5 Hz, H-2), 3.63–3.58 (m, 1H, H-5), 3.44–3.41 (m, 1H, H-4), 3.39 (s, 3H, $O_{Me}$), 2.09 (s, 3H, Ac). HRMS calc. for C₁₇H₁₅Cl₄NNaO₈ (M+Na): 523.9449; found: 523.9447.

Methyl 4-O-(2,4,6-tri-O-acetyl-3-azido-3-deoxy-δ-D-galactopyranosyl)-6-O-acetyl-2-deoxy-2-tetrachlorophthalimido-β-D-glucopyranoside (8). Compounds 5 (66.1 mg, 0.183 mmol), 7 (76.9 mg, 0.153 mmol), and activated molecular sieves AW-300 (0.35 g) were stirred in dry CH$_2$Cl$_2$ (5.0 mL) for 30 minutes with under nitrogen atmosphere. The mixture was cooled to −42° C. and N-iodosuccinimide (51.2 mg, 0.228 mmol) was added followed by trifluoromethanesulfonic acid (2.0 µL, 22.6 µmol). The reaction mixture was allowed to reach room temperature after 2 hours, filtered, and diluted with CH$_2$Cl$_2$. The organic layer was washed with 10% aqueous Na$_2$S$_2$O$_3$, dried over MgSO$_4$, filtered, and concentrated. The residue was chromatographed (SiO$_2$, 2:1 heptane-ethylacetate) to give 8 (93.9 mg, 75%), $[\alpha]_D^{25}$ +7.6° (c 1.0, CHCl$_3$). $^1$H-NMR data (400 MHz, CDCl$_3$) δ 5.36 (d, 1H, J=3.1 Hz, H-3), 5.15 (q, 1H, J=10.6, 7.9 Hz, H-2), 5.10 (d, 1H, J=8.5 Hz, H-1'), 4.52 (d, 1H, J=7.9 Hz, H-1), 4.35–4.29 (m, 1H, H-3'), 4.28 (d, 1H, J=1.3 Hz, H-4'), 4.06–4.14 (m, 3H, H-6,2',6'), 3.88–3.99 (m, 2H, H-5, 6), 3.70 (m, 1H, H-5'), 3.59 (q, 1H, J=10.6, 3.4 Hz, H-3), 3.53 (d, 1H, J=8.2 Hz, H-6'), 3.42 (s, 3H, OMe), 2.15, 2.13, 2.12, 1.90 (4 s, 3H each, Ac). HRMS calc. for C$_{29}$H$_{30}$Cl$_4$N$_4$NaO$_{15}$ (M+Na): 837.0359; found: 837.0374.

Methyl (2,4,6-tri-O-acetyl-3-azido-3-deoxy-β-D-glucopyranosyl)-2-acetamido-6-O-acetyl-2-deoxy-β-D-glucopyranoside (9). Dry diaminoethane (18 µL) was added to a solution of 8 (133 mg, 0.152 mmol) in dry EtOH (13 The mixture was heated at 60° C. for 7.5 hours then co-concentrated with toluene (5 mL). The residue was dissolved in MeOH (15 mL), H$_2$O (3 mL), and AC$_2$O (4.5 mL), stirred over night, then co-concentrated with toluene (20 mL). The residue was chromatographed (SiO$_2$, 1:1 toluene-acetone) to give 9 (70.6 mg, 83%), $[\alpha]_D^{25}$ +1.6° (c 0.03, CHCl$_3$). $^1$H-NMR data (400 MHz, CDCl$_3$) δ (d, 1H, J=7.8 Hz, is NH), 5.40 (d, 1H, J=3.3 Hz, H-4'), 5.17 (dd, 1H, J=10.6, 8.0 Hz, H-2'), 4.62 (d, 1H, J=8.3 Hz, H-1), 4.54 (d, 1H, J=8.0 Hz, H-1'), 4.34–4.31 (m, 2H, OH, H-6), 4.18 (dd, 1H, J=10.7, 3.7 Hz, H-6'), 4.09–3.93 (m, 4H, H-6, 5', 3, 6'), 3.62–3.57 (m, 2H, H-5,3'), 3.48 (s, 3H, OMe), 3.51–3.44 (m, 2H, H-4,2), 2.17, 2.16, 2.11, 2.06, 2.01 (5 s, 3H each, Ac). HRMS calc. for C$_{23}$H$_{34}$N$_4$NaO$_{14}$ (M+Na): 613,1969; found: 613.1972.

Methyl 4-O-(2,4, 6-tri-O-acetyl-2–3-azido-3-deoxy-β-D-galactopyranosyl)-2-acetamido-6-O-acetyl-2-dexy-3-O-stearoyl-β-D-glucopyranoside (10). To a solution of 9 (65.9 m, 0.112 mmol), pyridine (0.45 mL) and DMAP (cat.) in dry CH$_2$Cl$_2$ (10 mL) under nitrogen atmosphere, was added stearoyl chloride (0.160 mL, 0.475 mmol) at −78° C. The mixture was allowed to reach room temperature, then quenched with EtOH (2 mL) after 24 hours and concentrated. The residue was chromatographed (SiO$_2$, 3:1 toluene-acetone) to give 10 (75.8 mg, 79%), $[\alpha]_D^{25}$ −16.4° (c 1.0, CHCl$_3$). $^1$H-NMR data (400 MHZ, CDCl$_3$) δ 5.72 (d, 1H, J=9.5 Hz, NH), 5.39 (d, 1H, J=3.3 Hz, H-4'), 5.07–5.02 (m, 2H, H-2',3), 4.46 (dd, 1H, J=11.9, 8.9 Hz, H-6), 4.44 (d, 1H, J=7.9 Hz, H-1'), 4.33 (d, 1H, J=7.2 Hz, H-1), 4.19 (dd, 1H, J=11.9, 5.4 Hz, H-6), 4.08–4.03 (m, 3H, H-2, 6', 6'), 3.85–3.82 (m, 1H, H-5'), 3.74(t, 1H, J=8.1 Hz, H-4), 3.66–3.61 (m, 1H, H-5'), 3.58 (dd, 1H, J=10.6, 3.4 Hz, H-3'), 3.44 (3, 3H, OMe), 2.28 (t, 2H, J=7.6 Hz, —COCH$_2$—) 2.14, 2.12, 2.11, 2.06, 1.95 (5 s, 3H, Ac), 1.51–1.64 (m, 2H, —COCH$_2$CH$_2$—), 1.23 (bs, 28H, —CH$_2$—), 0.88–0.85 (m, 3H, CH$_3$). HRMS calc. for C$_{41}$H$_{68}$N$_4$NaO$_{15}$ (M+Na): 879, 4579; found: 879.4596.

Synthesis of Inhibitors 12–24 (Table 1 Above).

The galectin-3 inhibitors 12–24 of this invention are typically prepared by reaction of a methyl 4-O-(2,4,6-tri-O-acetyl-3-amino-3-deoxy-β-D-galactopyranosyl)-2-acetamido-6-O-acetyl-2-deoxy-3-O-stearoyl-β-D-glucopyranoside 11 with carboxylic acid halides, anhydrides, sulfonyl halides, isocyanates or amino acid derivatives according to examples A and B below:

Example A

Typical procedure for acylations ad sulfonylations (Synthesis of compounds 12–22). To a solution of 10 (29.0 mg, 38.8 µmol) in EtOH (degassed, 20 mL), was added 1M HCl (0.34 mL, 0.34 mmol) and Pd/C (10%, 33.5 mg). The mixture was hydrogenated (H$_2$, 1 atm) for 20 minutes, filtered through Celite, and concentrated without heating to give the crude intermediate amine 11, which was immediately used without further purification. The crude 11 was dissolved in dry CH$_2$Cl$_2$ (10 mL)). Pentafluorobenzoyl chloride (49 µL, 0.34 mmol) and pyridine (15 µL, 0.19 mmol) were added under nitrogen atmosphere. The reaction was monitored by TLC and the reaction mixture was concentrated when 11 was consumed. The residue was dissolved in 70% MeOH and applied onto C18 silica (3 g). Excess reagents and impurities were washed away with 70% MeOH, whereafter elution with 100% MeOH gave a protected intermediate (31.2 mg, 90%) after concentration. The residue was dissolved in MeOH (4.0 mL) and 1 M NaOMe (0.6 mL) was added. The reaction was continued overnight and then neutralized with Duolite C436 (H$^+$) resin, filtered, and concentrated. The residue was dissolved in water and applied onto C18 silica (3 g). Excess reagents and impurities were washed away with water, whereafter elution with 30% MeOH gave 18 (16.5 mg, 92%). The products were characterized with $^1$H-nmr spectroscopy, MALDI-TOF and HRMS-FAB mass spectrometri (Table 1).

Example B

Typical procedure for acylation with amino acids (Synthesis of compounds 23 and 24). To a solution of 10 (11.3 mg, 13.2 µmol) in EtOH (degassed, 20 mL), was added 1M HCl (0.135 mL, 0.135 mmol) and Pd/C (10%, 12.0 mg) The mixture was hydrogenated (H$_2$, 1 atm) for 20 minutes, filtered through Celite, and concentrated without heating to give the crude intermediate amine 11, which was immediately used without further purification. A solution of N-Boc-glycine (9.0 mg, 51.4 µmol) in dry CH$_2$Cl$_2$ (8 mL) was added to the crude 11 under nitrogen atmosphere, followed by N,N'-diisopropylcarbodiimide (10 µL, 64.6 µmol) and pyridine (15 µL, 0.19 mmol). The reaction was kept at room temperature overnight then co-concentrated with toluene under reduced pressure. The residue was dissolved in 70% MeOH and applied onto C18 silica (3 g). Excess reagents and impurities were washed away with 70% MeOH, whereafter elution with 100% MeOH gave a protected intermediate (13.1 mg, quantitative) after concentration. To the residue in dry CH$_2$Cl$_2$ (5.0 mL) was added TFA (0.5 mL). The reaction was co-concentrated with toluene (15 mL) after 5 hours and the residue was purified by C-18 solid-phase extraction as described above. The residue was dissolved in MeOH (4.0 mL) and NaOMe (0.6 mL, 1 M) was added and the reaction was left overnight, neutralized with Amberlite IR-120 (H$^+$) resin, filtered, and concentrated. The residue was dissolved in water and applied onto C18 silica (3 g) and elution with water gave 23 (4.1 mg, 84%). The products 23 and 24 were characterized with $^1$H-nmr spectroscopy, MALDI-TOF and HRMS-FAB mass spectrometry (Table 1).

Inhibition of Galectin-3 Binding to Galα3Galβ4GlcNAcβ-HRP Conjugate

The compounds prepared above (12–24) were tested for their ability to inhibiting the binding of galectin-3 to a Galα3Galβ4GlcNAcβ trisaccharide:horseradish peroxidase conjugate.

Screening experiments. Microtiter plate wells were coated with recombinant galectin-3 (10 μg/ml, 50 μl/well) from *E. coli* at 4° C. overnight, then washed three times with PBS-T. The wells were blocked with PBSA-T (100 μl/well) for 1 hour at room temperature, followed by washing with PBS-T. Compounds 12–25 (100 μL/well, 0.2 and 0.04 mM in PBS-T) were added in duplicate to the wells, followed by Galα3Galβ4GlcNAcβ-HRP conjugate (100 μL/well, 1 mg/mL in PBSA-T). The wells were washed with PBS-T after 1 hour incubation at room temperature; followed by development with the TMB-peroxidase substrate kit. The reaction was stopped after 60 min by addition of 1N sulfuric acid (100 μL/well) and optical density was read at 450 nm. Each experiment was conducted twice with each sample in duplicate. The pH of all the compound stock solutions were checked before testing and were all shown to be 7.1. $IC_{50}$ determinations for compounds 16, 18–19 and 25. Microtiter plate wells were coated with recombinant galectin-3 (10 μg/ml, 50 μl/well) from *E. coli* at 4° C. overnight, then washed three times with PBS-T. The wells were blocked with PBSA-T (100 μl/well) for 1 hour at room temperature, followed by washing with PBS-T. To the first well was added 125 μL of inhibitors 16, 18–19and 25 (0.2 mM in PBS-T). A five-fold serial dilution was performed by transfering 25 μL from the first well to a second well containing 100 μL PBS-T, mixing, then transfering 25 μL from the second well to a third well also containing 100 μL PBS-T, and so on to the eight well from which 25 μL were discarded. The dilution series was done in duplicate. Only PBS-T (100 μL) was added to one column of wells (in order to give the OD in the absence of inhibitor), as well as to one column of well not coated with galectin-3 (in order to give the background signal) To each well was then added Galα3Galβ4GlcNAcβ-HRP conjugate (100 μL/well, 1 mg/mL in PBS-T). Incubation, washing, and detection was performed as described above. The data was analyzed with non-linear regression analysis using the program Kaleidagraph™ from Synergy Software.

The results of this assay evidenced that the compounds 16–19 inhibited binding of galectin-3 to Galα3Galβ4GlcNAcβ-HRP conjugate with $IC_{50}$-values less than 50 μM.

From the foregoing description, various modifications and changes in the composition and method will occur to those skilled in the art. All such modifications coming within the scope of the appended claims are intended to be included therein.

Examples of the in vivo Efficacy of Galectin-3 Inhibition in Inflammation and Cancer.

Inflammation.

As mentioned above many studies suggest a role of galectin-3 in enhancing the inflammatory response. For example the addition of galectin-3 to neutrophil leukocytes from an inflammatory site, or primed by exposure to LPS, results in increased generation of toxic oxygen radicals. Lactose can inhibit this response (Karlsson et al., 1998; Almquist et al., 2001). In another study (Sano et al., 2000), galectin-3 was found to be chemotactic to macrophages and monocytes both in vitro and in vivo. Either lactose or the isolated CRD of galectin-3 (galectin 3C), able to bind the same saccharide receptor as galectin-3 but not cross link it (see below), acted as inhibitors of this response. The substances described in the present invention would be much more effective as inhibitors of the above mentioned responses than lactose because they are much more potent galectin-3 inhibitors. They would also be much more usable in vivo than lactose and the galectin-3C because they are small molecules, more hydrophobic and probably more stable to degradation.

Cancer.

As mentioned above, several studies of models of human cancer in mice indicate that enhanced expression of galectin-3 results in faster tumor growth and more metastasis (Bresalier et al., 1998; reviewed by Leffler, 2001). Injection of a saccharide with inhibitory potency to galectin-3, but perhaps also other proteins, was reported to diminish prostate cancer in rat (Pienta et al., 1995). Hence, potent small molecule inhibitors of galectin-3 are expected to have similar anticancer effects as galectin-3C.

REFERENCES

Almkvist, J., Fäldt, J., Dahlgren, C., Leffler, H., and Karlsson, A. (2001) Lipopolysaccharide-induced gelatinase granule mobilization primes neutrophils for activation by galectin-3 and f-Met-Leu-Phe. *Infect. Immun.* Vol. 69: 832–837.

André, S., Ortega, P. J. C., Perez, M. A., Roy, R., and Gabius, H.-J.(1999) Lactose-containing starburst dendrimers: influence of dendrimer generation and binding-site orientation of receptors (plant/animal lectins and immunoglobulins) on binding properties. *Glycobiology* 11:1253–1262.

Barondes, S. H., Cooper, D. N. W., Gitt, M. A., and Leffler, H. (1994). Galectins. Structure and function of a large family of animal lectins. *J. Biol. Chem.* 269:20807–20810.

Bresalier, R. S., Mazurek, N., Sternberg, L. R., Byrd, J. C., Yunker, C. K., Nangia-Makker, P., Raz, A. (1998) Metastasis of human colon cancer is altered by modifying expression of the beta-galactoside-binding protein galectin 3. *Gastroenterology* 115:287–296.

Cooper, D. N. and Barondes, S. H. (1999) God must love galectins; he made so many of them. *Glycobiology* 9:979–984.

Glinsky, G. V., Price, J. E., Glinsky, V. V., Mossine, V. V., Kiriakova, G., Metcalf, J. B. (1996) Inhibition of human breast cancer metastasis in nude mice by synthetic glycoamines. *Cancer Res.* 56:5319–5324.

Helland, A.-C., Hindsgaul, O., Palcic, M. M., Stults, C. L. M., Macher, B. A. (1995) Methyl 3-amino-3-deoxy-β-D-galactopyranosyl-(1-4)-2-acetamido-2-deoxy-β-D-glucopyranoside: an inhibitor of UDP-D-galactose:β-D-galactopyranosyl-(1-4)-2-acetamido-2-deoxy-D-glucose (1-3)-α-D-galactopyranosyltransferase. *Carbohydr. Res.* 276:91–98.

Hsu, D. K., Yang, R. Y., Pan, Z., Yu, L., Salomon, D. R., Fung-Leung, W. P., Liu, F. T. (2000) Targeted disruption of the galectin-3 gene results in attenuated peritoneal inflammatory responses. *Am. J. Pathol.* 156:1073–1083.

Karima, R., Matsumoto, S., Higashi, H., Matsushima, K. (1999) The molecular pathogenesis of Endotoxic Shock and Organ Failure. *Molecular Medicine Today* 5:123–132.

Karlsson, A., Follin, P, Leffler, H., Dahlgren, C. (1998) Galectin-3 activates the NADPH-oxidase in exudated but not peripheral blood neutrophils. *Blood* 91:3430–3438.

Leffler, H. and Barondes, S. H. (1986) Specificity of binding of three soluble rat lung lectins to substituted and unsubstituted mammalian beta-galactosides. *J. Biol. Chem.* 261: 10119–10126.

Leffler, H. Galectins Structure and Function—A Synopsis in Mammalian Carbohydrate Recognition Systems (Crocker, P. ed.) Springer Verlag, Heidelberg, 2001 pp. 57–83.

Lobsanov, Y. D. and Rini, J. M. (1997) Galectin Structure. *Trends. Glycosci. Glycotech.* 45:145–154.

Lowary, T. L. and Hindsgaul, O. (1994) Recognition of synthetic O-methyl, epimeric, and amino analogues of the acceptor α-L-Fucp-(1-2)-β-D-Galp-OR by the blood-group A and B gene-specified glycosyltransferases. *Carbohydr. Res.* 251:33–67.

Massa, S. M., Cooper, D. N. W., Leffler, H., Barondes, S. H. (199) L-29, an endogenous lectin, binds to glycoconjugate ligands with positive cooperativity. *Biochemistry* 32; 260–267.

Naidenko, O., Kronenberg, M., Glinsky, G., and Huflejt, M. E. (2000) Interaction of galectins with low molecular weight lactosylaminoconjugates. *Glycobiology* 10:abstract 60.

Perillo, N. L., Marcus M. E., and Baum, L. G. (1998) Galectins: versatile modulators of cell adhesion, cell proliferation, and cell death. *J. Mol. Med.* 76:402–412.

Pienta, K. J., Naik, H., Akhtar, A., Yamazaki, K., Replogle, T. S., Lehr, J., Donat, T. L., Tait, L., Hogan, V., Raz, A. (1995) Inhibition of spontaneous metastasis in a rat prostate cancer model by oral administration of modified citrus pectin. *J. Natl. Cancer Inst.* 87:348–353

Pohl, N. L. and Kiessling, L. L. (1999) Scope of multivalent ligand function: Lactose-bearing neoglycopolymers by ring-opening metathesis polymerization. *Synthesis* 1515–1519.

Sano, H., Hsu, D. K., Yu, L., Apgar, J. R., Kuwabara, I., Yamanaka, T., Hirashima, M., Liu, F. T. (2000) Human galectin-3 is a novel chemoattractant for monocytes and macrophages. *J. Immunol.* 165:2156–2164.

Seetharaman, J., Kanigsberg, A., Slaaby, R., Leffler, H., Barondes, S. H., Rini, J. M. (1998) X-ray crystal structure of the human galectin-3 carbohydrate recognition domain at 2.1-A resolution. *J. Biol. Chem.* 273:13047–13052.

Stangier, P. and Hindsgaul, O. (1996) Solid-Phase Transimidation for the Removal of N-Phthalimido- and N-Tetrachlorophthalimido Protecting Groups on Carbohydrates. *Synlett* 179–181.

Trahey, M. and Weissman, I. L. (1999) Cyclophilin C-associated protein: a normal secreted glycoprotein that dow-modulates endotoxin and proinflammatory responses in vivo. *Proc. Natl. Acad. Sci. USA* 96:3006–3011.

The invention claimed is:

1. A compound having the general formula (I):

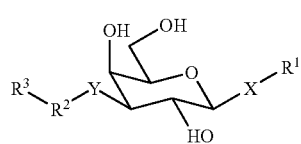

(I)

wherein the configuration of the pyranose ring is D-galacto;

X is selected from the group consisting of O, S, NH, $CH_2$, and $NR^4$, or is a bond;

Y is selected from the group consisting of NH, $CH_2$, and $NR^4$, or is a bond;

$R^1$ is selected from the group consisting of: a saccharide, hydrogen, an alkyl group, an alkenyl group, and an aryl group;

$R^2$ is selected from the group consisting of CO, $SO_2$, SO, PO, and $PO_2$;

$R^3$ is selected from the group consisting of;

a) an alkyl group of at least 4 carbon atoms, an alkenyl group of at least 4 carbon atoms, an alkyl or alkenyl group of at least 4 carbon atoms substituted with a carboxy group, an alkyl group of at least 4 carbon atoms substituted with both a carboxy group and an amino group, and an alkyl group of at least 4 carbon atoms substituted with a halogen;

b) a phenyl group, a phenyl group substituted with a carboxy group, a phenyl group substituted with at least one halogen, a phenyl group substituted with an alkoxy group, a phenyl group substituted with at least one halogen and at least one carboxy group, a phenyl group substituted with at least one halogen and at least one alkoxy group, a phenyl group substituted with a nitro group, a phenyl group substituted with a sulfo group, a phenyl group substituted with an amine group, a phenyl group substituted with a hydroxy group, a phenyl group substituted with a carbonyl group and a phenyl group substituted with a substituted carbonyl group; and c) a phenyl amino group; and $R^4$ is selected from the group consisting of hydrogen, an alkyl group, an alkenyl group, and an aryl group.

2. A compound according to claim 1, wherein $R^1$ is a saccharide and is selected from the group consisting of glucose, mannose, galactose, N-acetylglucosamine, N-acetylgalactosamine, fucose, fructose, xylose, sialic acid, glucoronic acid, iduronic acid, a disaccharide or, an oligosaccharide comprising at least two of the above saccharides, and derivatives thereof.

3. A compound according to claim 1 or 2, wherein Y is NH.

4. A compound according to claim 1, wherein X is O.

5. A compound according to claim 1, wherein said halogen is selected from the group consisting of F, Cl, Br and I.

6. A compound-according to claim 1, wherein said compound is methyl 2-acetamido-2-deoxy-4-O-(3-[3-carboxypropanamido]-3-deoxy-∃-D-galactopyranosyl)-β-D-glucopyranoside, methyl 2-acetamido-2-deoxy-4-O-(3-[{Z}-3-carboxypropenamido]-3-deoxy-β-D-galactopyranosyl)-β-D-glucopyranoside, methyl 2-acetamido-2-deoxy-4-O-(3-benzamido-3-deoxy-β-D-galactopyranosyl)-β-D-glucopyranoside, methyl 2-acetamido-2-deoxy-4-O-(3-[2-carboxybenzamido]-3-deoxy-β-D-galactopyranosyl)-β-D-glucopyranoside, methyl 2-acetamido-2-deoxy-4-O-(3-[4-methoxy-2,3,5,6-tetrafluorbenzamido]-3-deoxy-β-D-galactopyranosyl)-β-D-glucopyranoside, methyl 2-acetamido-2-deoxy-4-O-(3-[2-carboxy-3,4,5,6-tetrafluorbenzamido]-3-deoxy-β-D-galactopyranosyl)-β-D-glucopyranoside, methyl 2-acetamido-2-deoxy-4-O-(3-[4-nitroben zenesulfonamido]-3-deoxy-β-D-galactopyranosyl)-β-D-glucopyranoside, methyl 2-acetamido-2-deoxy-4-O-(3-phenylaminocarbonylamino-3-deoxy-β-D-galactopyranosyl)-β-D-glucopyranoside, methyl 2-acetamido-2-deoxy-4-O-(3-[{2S}-2-amino-3-carboxy-propanamido]-3-deoxy-β-D-galactopyranosyl)-β-D-glucopyranoside.

7. A pharmaceutical composition comprising a compound according to claim 1, as the active ingredient together with a pharmaceutically acceptable adjuvant, diluent, excepient or carrier.

8. A pharmaceutical composition according to claim 7, comprising from 1 to 99 weight % of a pharmaceutically acceptable adjuvant, diluent, excepient or carrier and from 1 to 99 weight % of a compound.

* * * * *

UNITED STATES PATENT AND TRADEMARK OFFICE
CERTIFICATE OF CORRECTION

PATENT NO. : 7,230,096 B2  Page 1 of 1
APPLICATION NO. : 10/466933
DATED : June 12, 2007
INVENTOR(S) : Ulf Nilsson et al.

It is certified that error appears in the above-identified patent and that said Letters Patent is hereby corrected as shown below:

In claim 1, column 24, line 7, "of: a" should read --of a--.

In claim 2, column 24, line 43, "or, an" should read --or an--.

In claim 6, column 24, line 52, "compound-according" should read --compound according--.

In claim 6, column 24, lines 53-55, "2-acetamido-2-deoxy-4-O-(3-[3-carboxypropanamido]-3-deoxy-∃ -D-galactopyranosyl)-β-D-glucopyranoside," should read --2-acetamido-2-deoxy-4-O-(3-[3-carboxypropanamido]-3-deoxy-β-D-galactopyranosyl)-β-D-glucopyranoside,--.

In claim 6, column 24, line 67 through column 25, line 2, "2-acetamido-2-deoxy-4-O-(3-[4-nitroben zenesulfonamido]-3-deoxy-β-D-galactopyranosyl)-β-D-glucopyranoside," should read --2-acetamido-2-deoxy-4-O-(3-[4-nitrobenzenesulfonamido]-3-deoxy-β-D-galactopyranosyl)-β-D-glucopyranoside,--.

In claim 8, column 26, line 4, "a" should read --the--.

*In claim 8, column 26, line 6, "a" should read --the--.

Signed and Sealed this

Fifteenth Day of July, 2008

JON W. DUDAS
*Director of the United States Patent and Trademark Office*